US006998978B2

(12) United States Patent
Kirkeby

(10) Patent No.: US 6,998,978 B2
(45) Date of Patent: Feb. 14, 2006

(54) METHOD AND APPARATUS FOR RESPONDING TO MEDICAL ALERTS

(75) Inventor: Kevin Wayne Kirkeby, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 128 days.

(21) Appl. No.: 10/835,463

(22) Filed: Apr. 29, 2004

(65) Prior Publication Data

US 2005/0242928 A1   Nov. 3, 2005

(51) Int. Cl.
   *G08B 1/08*   (2006.01)
(52) U.S. Cl. .............................. 340/539.12; 340/539.11; 340/539.13; 340/539.18; 340/686.1; 340/686.6; 340/573.1; 340/7.5; 340/7.55; 340/7.2; 600/515; 600/518
(58) Field of Classification Search ................ 600/515, 600/518; 340/7.2, 7.55, 7.5, 573.1, 686.6, 340/686.1, 539.18, 539.13, 539.11, 539.12
   See application file for complete search history.

(56) References Cited

U.S. PATENT DOCUMENTS 5,874,897 A * 2/1999 Klempau et al. ......... 340/573.1
6,292,687 B1 * 9/2001 Lowell et al. .............. 600/515

OTHER PUBLICATIONS

Kiran Thapa, et al., "An Indoor Positioning Service for Bluetooth Ad Hoc Networks", Department of Computer & Information Sciences, Minnesota State University, Mankato.
Abhishek Patil, "Performance of Bluetooth Technologies and Their Applications to Location Sensing", A Thesis, Submitted to Michigan State University Department of Electrical and Computer, 2002, pp. 1-81.
http://www.medhost.com/_products-tracking.asp, "Benefits of EDMS Tracking", Sep. 3, 2003, p. 1.
http://www.symbol.com/solutions/healthcare/healthcare_ambulance.html, "Wireless Mobility: A Matter of Life and Death", Sep. 3, 2003, pp. 1-3.
http://www.safetypad.com/home.htm, "Safetypad. Prehospital data collection emergency medical information wearable computer", Sep. 3, 2003, p. 1.
http://www.gwhospital.com/p5582.html, "Wireless Network/Palm Pilots", Sep. 3, 2003, p. 1.
http://www.healthcare-informatics.com/issues/2001/09_01/baldwin.htm, "Healthcare Informatics: Book 'em", Sep. 24, 2003, pp. 1-9.
Becker, et al., "OntHoS—an Ontology for Hospital Scenarios".
Sackmann, et al, "EMIKA—Real-Time Controlled Mobile Information Systems in Health Care Applications", pp. 151-158.

(Continued)

*Primary Examiner*—Daniel Wu
*Assistant Examiner*—Tai T. Nguyen
(74) *Attorney, Agent, or Firm*—Grant A. Johnson

(57) ABSTRACT

A method, system, and article of manufacture for responding to medical alerts, one embodiment of which comprises receiving a medical alert having an associated alert location, detecting a current location for each of a plurality of medical staff members, and selecting a medical staff member to respond to the medical alert based at least in part on the distance between the alert location and the current location. Some embodiments may further comprise receiving a plurality of medical alerts, determining if any of the medical alerts indicates an emergency situation, generating a prioritized task from non-emergency alerts, and selecting a highest priority medical alert from the prioritized list.

19 Claims, 9 Drawing Sheets

OTHER PUBLICATIONS http://www.sensitron.net/technology/wirelessEnab.html, "The careTrends System", pp. 1-2, Jul. 16, 2004.

http://www.monitoring.welchallyn.com, "Welch Allyn Monitoring Systems", p. 1, Jul. 16, 2004.

Agder University College Faculty of Engineering and Science Institute of ICT, http://www.cs.auc.dk/WIM/workshop-02/AgderUniversityCollege.pdf,"Research Activities Related to WIM Topics", pp. 1-6.

http://katanga.bbn.de/mobile_europe_2003/pdf_programm/thu_ses_03_02_husemann.pdf, Open Mobile Phone Hub: Gateway to the World, Bridging between Near and Far, pp. 1-20, printed Jul. 16, 2004.

http://www.nexterna.com/field_service/data_sheets/NCV_Dispatch.pdf, "Nexterna Clearview", pp. 1-2.

http://www.omniwatchtech.com/Vislink.htm, "VisionLink Wireless Emergency Call System", pp. 1-2.

http://story.news.yahoo.com/news?tmpl=story&cid=528&e=1&u=/ap/20050330/ap_on_hi_te/sweden_ rem . . . ,"Wireless Device Can Monitor Patients", pp. 1-3, printed Mar. 31, 2005, date unknown.

* cited by examiner

| Request ID | Request Name | Initial Priority | List of Qualified Personnel | Required Equipment |
|---|---|---|---|---|
| 1 | Cardiac Arrest | 0 (Emergency) | D001, D002, D003 | M0015, M104 |
| 2 | Stopped Breathing | 0 (Emergency) | D001, D002, D003, D004, D005 | M010 |
| 3 | Stroke | 1 (Emergency) | | |
| .. | | | | |
| 50 | Monitor is Malfunctioning | 10 | M001, M002, M003, M004, M005 | |
| .. | | | | |
| 100 | Patient is too far from room | 30 | N001, N002, N003, OR001, OR002 | |
| .. | | | | |
| 130 | IV Bag empty | 50 | N001, N002, N003 | S004 |
| .. | | | | |
| 170 | Patient has vomited | 50 | N002, N003, N004 | |
| .. | | | | |
| 301 | Patient needs assistance to use the bathroom | 100 | N002, N003, N004, OR001, OR002 | |
| .. | | | | |

FIG. 6

| ID | Name | Current Priority | Location |
|---|---|---|---|
| D001 | J. Smith | 25 | 204W |
| D002 | M. Johnson | 0 | 605E |
| .. | | | |
| N001 | S. Jones | 0 | 605E |
| .. | | | |
| OR005 | J. Brown | 75 | 301W |
| .. | | | |
| M0015 | Defibrillator | 999 | 600L |
| .. | | | |

FIG. 7

METHOD AND APPARATUS FOR RESPONDING TO MEDICAL ALERTS

TECHNICAL FIELD

The present invention relates to methods and apparatus for responding to alerts. More specifically, the present invention relates to receiving, prioritizing, and assigning staff members to medical alerts.

BACKGROUND

Today's economic environment requires businesses to provide better service using fewer people. Medical facilities, such as hospitals, are no different. In some cases, this pressure is driven by a difficulty in finding qualified staff. In other cases, this pressure is driven by competition and insurance companies. Unfortunately, the relentless pressure to cut costs can conflict with the basic mission of a hospital—to provide comfort to the patients and their loved ones.

Currently, when medical devices require human interaction from medical personnel, the medical device generates an alarm to alert nearby nurses and doctors. For example, when a patient's intravenous ("I.V.") fluid drip bag goes empty, the I.V. machine generates an alarm until someone resets the machine and gives the patient the necessary medication and fluids. Unfortunately, the medical staff members are often located several rooms away and are busy with other tasks, which means that the I.V. device will continue to generate the alarm for some time. These extended alarm messages disturb other patients and can lead to so-called information overload. These problems are compounded because, after a staff member finally responds to the alarm and diagnoses its cause, the staff member frequently needs to get the required supplies from a medicine cabinet and then return to the patient's room to perform the change.

Many hospitals have begun experimenting with wireless communication technology as a partial solution to this problem. As a result, many new medical devices include a wireless network interface that can notify the hospital staff when they need attention. This technology allows medical devices, such as I.V. machines, to notify the hospital's nursing staff when they are empty and electrocardiogram machines to notify a patient's doctor when the patient goes into cardiac arrest. Many hospitals also use wireless technology to allow patients to contact the hospital's staff whenever the patient needs assistance.

Although this technology has provided many benefits, it can impose a heavy load on an already overworked staff. That is, many hospitals are finding their staff members inundated with an almost constant stream of alerts from equipment and requests from patients. Without a way to prioritize all of the alerts and requests, and then smartly dispatch the closest, available, qualified staff person, the promise of wireless medical technology may never be fully achieved.

SUMMARY

The present invention provides a method, system, and article of manufacture that receives, prioritizes, and assigns staff to medical alerts. Accordingly, one aspect of the present invention is a method of responding to medical alerts comprising receiving a medical alert, the medical alert having an associated alert location, detecting a current location for each of a plurality of medical staff members, and selecting a medical staff member to respond to the medical alert based at least in part on the distance between the alert location and the current location. In some embodiments, this method may further comprise receiving a plurality of medical alert, determining if any of the medical alerts indicates an emergency situation, generating a prioritized task from non-emergency alerts, and selecting a highest priority medical alert from the prioritized list.

Another aspect of the present invention is a medical alert response system comprising a medical device that generates an alert message in response to an alert condition; a plurality of medical alert consoles that wirelessly communicates a current location for its associated medical staff member; and a dispatcher that receives the medical alert message from the medical device and the current locations from the plurality of medical alert consoles and selects a medical staff member to respond to the alert based on the proximity between the device location and the staff member's current location. In some embodiments, this medical alert response system also includes a patient console that wirelessly communicates a patient request and a patient location to the dispatcher in response to a patient input, and the medical alert consoles comprise a display screen adapted to communicate the medical device location, a medical alert type, and any necessary equipment and supplies to the associated medical staff member.

Another aspect of the present invention is a computer program product comprising a program configured to perform a method of assigning medical assets and a signal bearing media bearing the program. The method of assigning medical assets in some embodiments comprises receiving a medical alert, the medical alert having an associated alert location, detecting a current location for each of a plurality of medical staff members, and selecting a medical staff member to respond to the medical alert using the alert location and the current location. The signal bearing media in these embodiments may comprise information permanently stored on non-writable storage media, alterable information stored on writable storage media, and information conveyed to a computer by a communications medium.

BRIEF DESCRIPTION OF THE DRAWINGS

FIG. 6 depicts a configuration file embodiment for the central command computer.

FIG. 7 depicts a status tracking data structure embodiment for the medical personal and medical devices.

DETAILED DESCRIPTION

Figure 1:
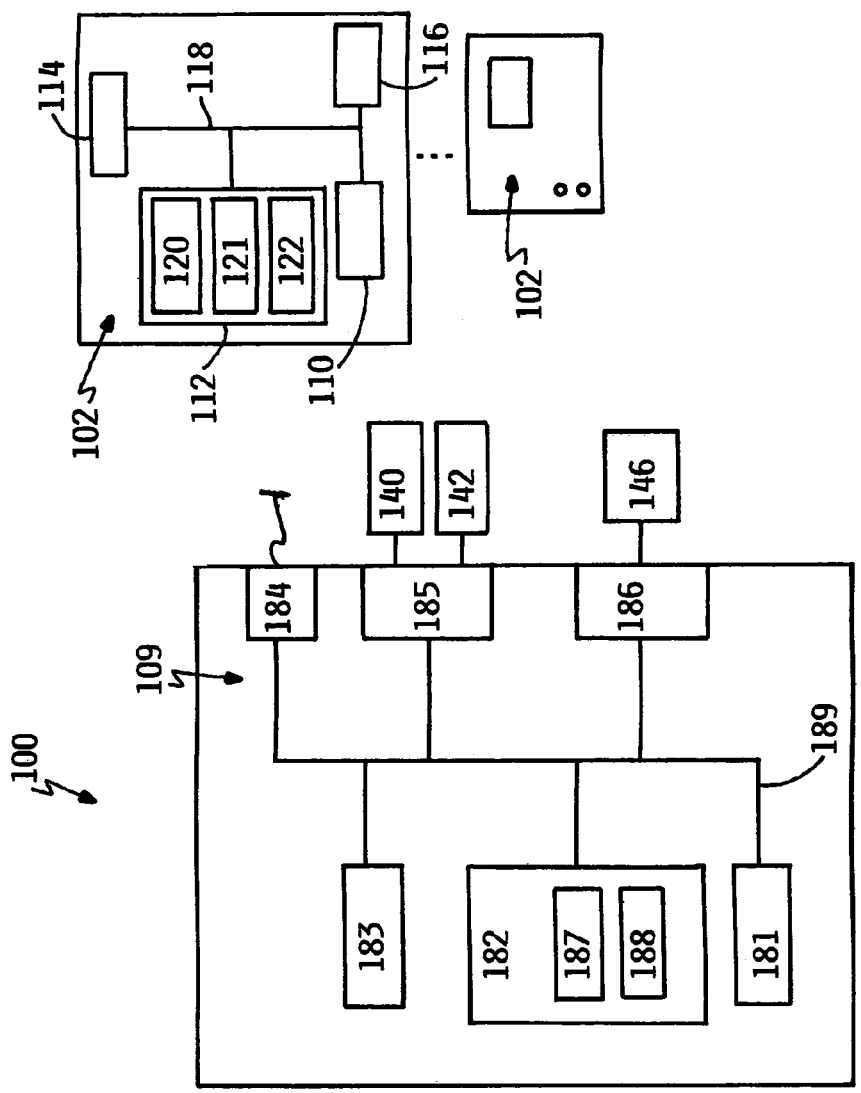
FIG. 1 depicts one embodiment of a medical dispatch system.

FIG. 1 depicts one embodiment of a medical dispatch system 100 comprising a plurality of medical devices 102, a plurality of mobile medical staff consoles 104, and a plurality of patient consoles 108. Each medical device 102 has a central processing unit 110 ("CPU") connected to a memory 112, a network interface 114, and a location detection unit 116 by a system bus 118. Each staff console 104 is carried by one of the hospital's medical staff and comprise a central processing unit 130 ("CPU") connected to a memory 132, a wireless network interface 134, a display 135, and a location detection unit 136 by a system bus 138. Each patient consoles 108 is carried by or located near a patient and comprises a central processing unit 170 ("CPU") connected to a memory 172, a network interface 174, an input device 175, and a location detection unit 176 by a system bus 178. The memory units in each of the medical devices 102, medical staff consoles 104, and patient consoles 108 contains an operating system 120, an identifier 121, and an alert management program 122. The medical dispatch system 100 also includes a central command computer 109, comprising a central processing unit 181 connected to a main memory unit 182, a wireless network interface 183, a wired network interface 184, a mass storage interface 185, and a display interface 186 by a system bus 189. The main memory 182 in the central command computer 109 contains an operating system 187 and a request management program 188. The central command computer 109 also includes a direct access storage device, such as a hard disk drive 140 or a CD-ROM drive 142, and a display 146.

In operation, the medical dispatch system 100 in FIG. 1 monitors requests from patients and alerts from medical devices, and then efficiently assigns available medical staff to handle these tasks based on the proximity of patient and qualified medical staff and the urgency of the request. For example, if one patient sends a request indicating that he or she is nauseated and a first medial device 102 (e.g., an IV machine) indicates that a second patient's IV bag just emptied, the medical dispatch system 100 will first determine whether either of these tasks are emergencies. If neither task is an emergency, the medical dispatch system 100 will then assign the tasks to one of its associated medical staff members, preferably to a staff member who is not otherwise occupied and/or in such a way as to allow that staff member to work on multiple tasks simultaneously. Later, if a second medical device 102 indicates that a third patient is going into cardiac arrest and a third medical device 102 indicates that a fourth patient's oxygen level is dangerously low, the medial dispatch system 100 will first determine that these alerts require urgent attention. The medical dispatch system 100 will then determine that the third alert (i.e., the cardiac arrest) has the highest priority and notify the closest qualified staff member about the third emergency, regardless of whether that staff member is already busy with another non-emergency, interruptible task. The medical dispatch system 100 will then recognize that the staff member responding to the third alert is busy with an uninterruptible task and alert the next closest qualified staff member about the fourth alert, again pulling medical staff members off lower priority tasks if necessary. After resolving the emergencies and tasks, the medical dispatch system 100 will then return the medical staff members back to a pool of people available to respond to requests.

Some embodiments of the present invention may also evaluate which medical staff member is closest to the necessary supplies and include a recommendation to get those supplies while in transit to the task location. Other embodiments may provide a logging mechanism that will help keep the nurses and doctors up-to-date with how their patients are being handled by the system 100 and that will alert future medical staff about recent events. This, in turn, allows for all medical staff to continually know what is going on instantaneously throughout their floor/ward and allow for them to take even better care of their patients.

Figure 2:
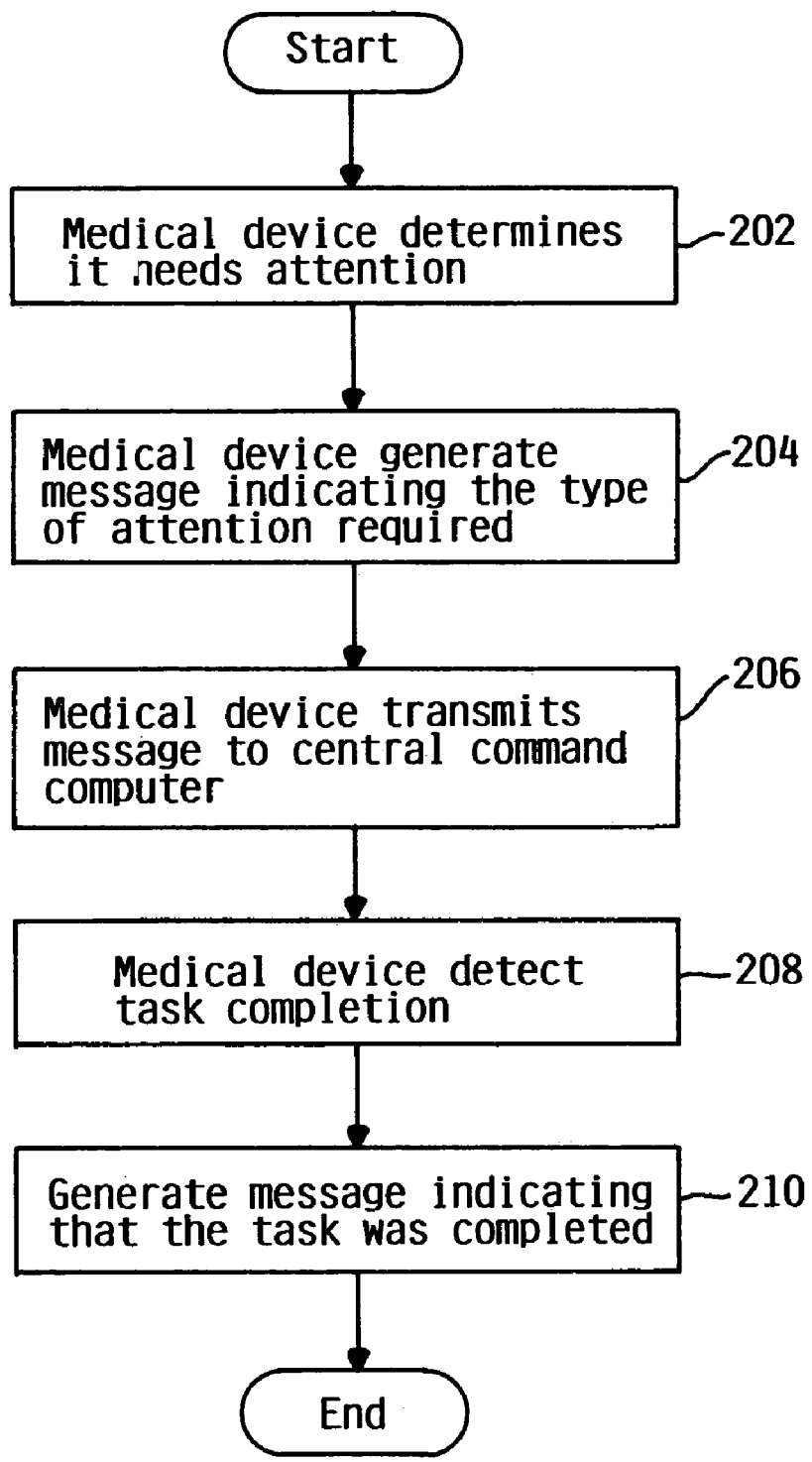
FIG. 2 illustrates the operation of the medical device embodiment in FIG. 1.

FIG. 2 illustrates the operation of one medical device 102 embodiment and its alert management program 122 in more detail. At block 202, the medical device 102 determines that it needs attention. This may occur because the device 102 needs attention or because the patient to which the medical device 102 is associated needs attention. At block 204, the medical device 102 generates a message containing its machine identifier and an event code (described in more detail with reference to FIG. 6) that indicates what type of attention is required. At block 206, the medical device 102 sends the message to the central command computer 109. In response, the central command computer 109 assigns a medial staff member to the task. After the assigned medical staff member completes the task, the medical device 102 determines that the event detected at block 202 has been resolved and sends a task completion message to the central computer 109 at blocks 208–210.

Figure 3:
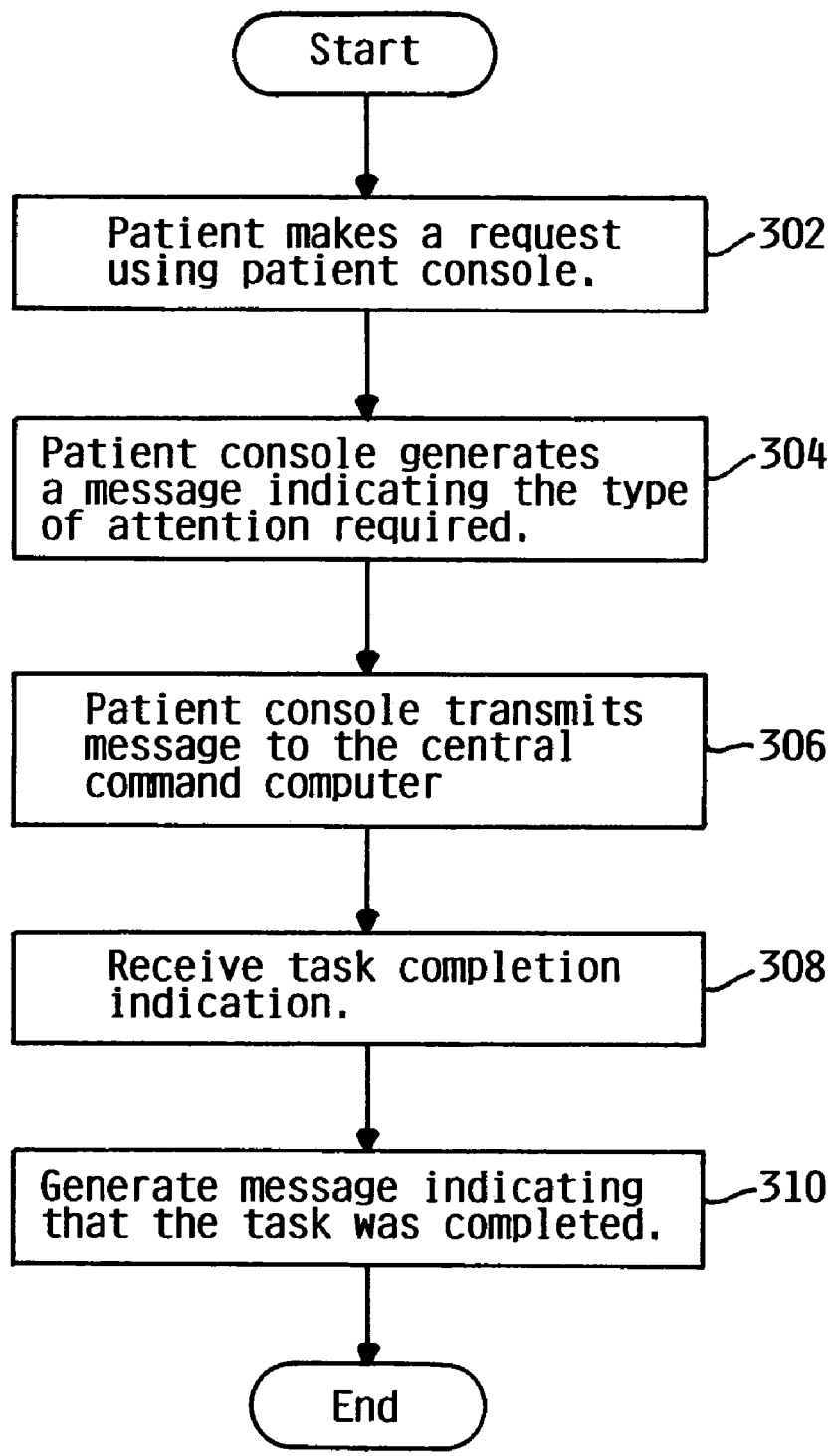
FIG. 3 illustrates the operation of the patient console embodiment in FIG. 1.

FIG. 3 illustrates the operation of one patient console embodiment 108 and its alert management program 122 in more detail. At block 302, the patient requests attention from the hospital's medical staff using their patient console 108. In some embodiments, this indication may include the reason for the request (i.e., bathroom, chest pains, etc) and/or the urgency. In other embodiments, this indication may be a simple on-off indication. At block 304, the patient console 108 generates a message containing a patient location and an event code (described in more detail with reference to FIG. 6) indicating that the patient needs attention and, if available, the reason and urgency of the request. At block 306, the patient console 108 sends the message to the central command computer 109. In response, the central command computer assigns a medical staff member to the task. At blocks 308–310, the patient or responding medical staff member indicates that the request has been satisfied and sends a task completion message to the central command computer 109.

Figure 4A:
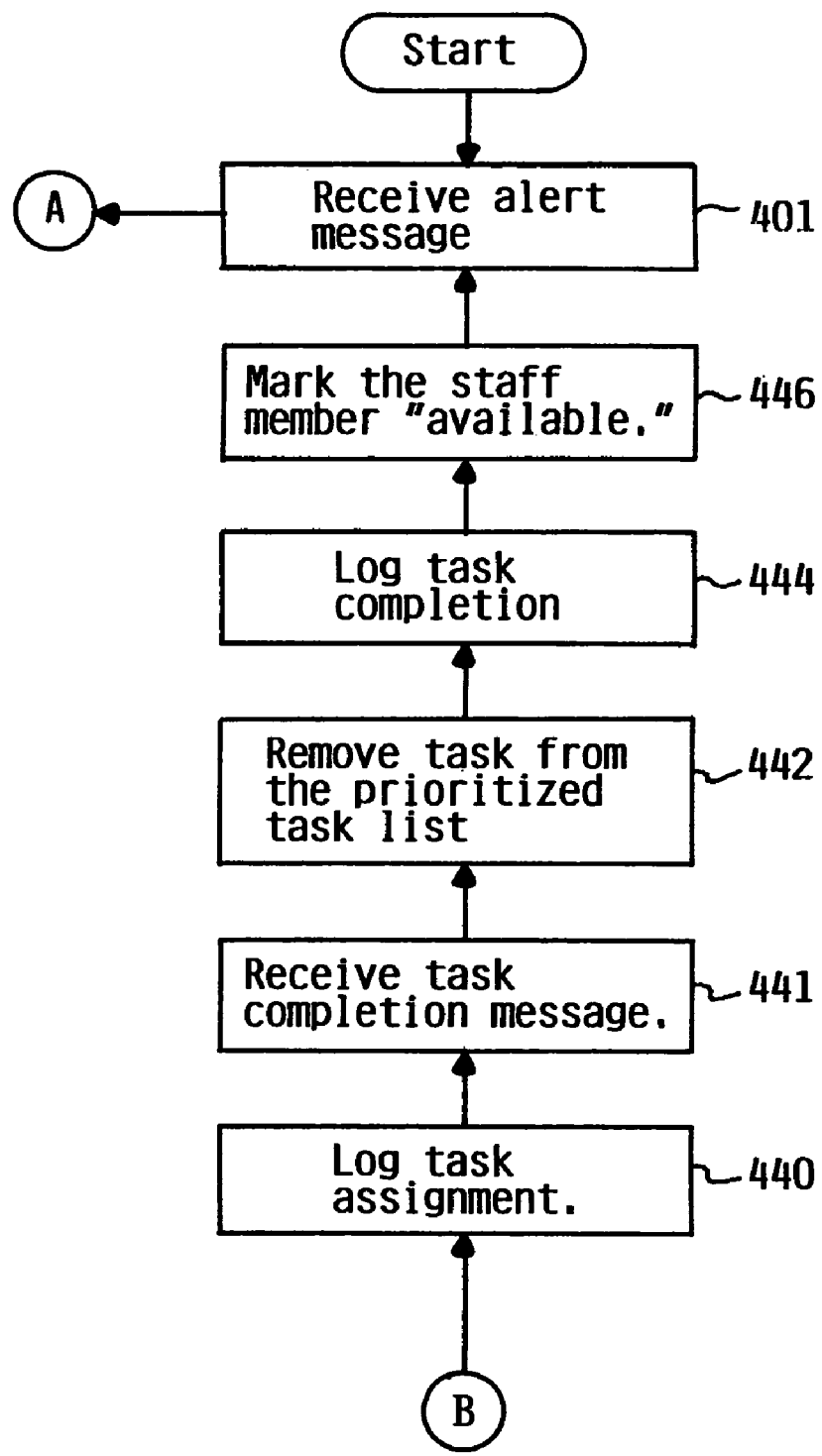
FIG. 4 illustrates the operation of the central command computer embodiment in FIG. 1.
Figure 4B:
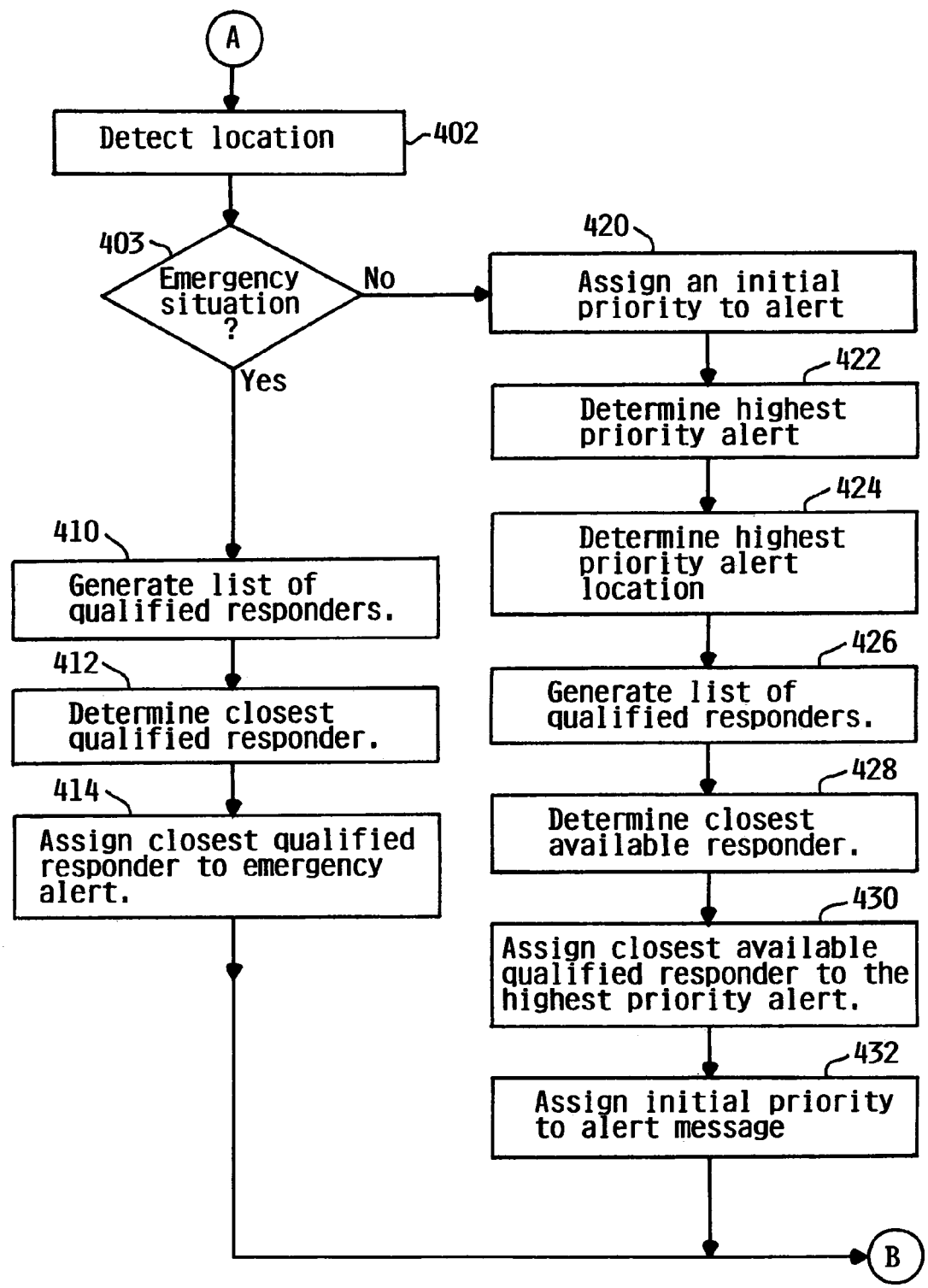

FIG. 4 illustrates the operation of the central command computer 109 and its alert management program 188 in more detail. At block 401, the central command computer 109 receives a message indicating that a patient or medical device needs attention. At block 402, the central command computer 109 determines the physical location from which the alert originated. The location detection in block 402 may occur in response to receiving the alert or may be detected as part of a periodic location polling system.

At block 403, the central command computer 109 determines whether the message indicates an emergency situation. If the message indicates that there is an emergency, the central command computer 109 generates a list of qualified medical staff members (e.g., any doctor, any nurse, or a specialist) at block 410. One suitable way of making this determination involves matching the event code sent at blocks 206 and 306 with a list of qualified people identified in the configuration file described in more detail with reference to FIG. 6. The central command computer 109 then determines the closest qualified medical staff member at block 412 and assigns that staff member at block 414. In some embodiments, the central command computer 109 may also keep an emergency task list (not shown) to prioritize the response to multiple emergency situations.

If the central command computer 109 determined at block 403 that the message was not associated with an emergency, the central command computer 109 then determines at block 420 the priority of the new request using the event codes sent at blocks 206 and 306 relative to any outstanding and/or in progress tasks. At block 422, the central command computer 109 selects the highest priority message still outstanding. The central command computer 109 then determines the location of the highest priority request at block 424, generates a list of qualified medical staff members at block 426, determines the closest available medical staff member at block 428, and assigns that medical staff member to the task at block 430. At block 432, the central command computer 109 then increases the priority of all of the unassigned requests in the queue. In some embodiments, these priority increases may be capped to prevent non-urgent requests from reaching emergency status. In some embodiments, the central command computer 109 may determine that a staff member can efficiently perform some tasks together and/or that some tasks may require common components (e.g., patient 1 and patient 2 both need medicine from a particular supply depot), group those tasks together into a common task, and then give the new, combined task the priority of the highest original task.

After assigning a medical staff member to respond to the alert, the central computer 109 will then log the assignment, together with its context, at block 440 in the journal described with reference to FIG. 8. The medical staff member then responds to the alert and resolves the problem. As discussed in more detail with reference to FIG. 5, the medical staff members can indicate that they have resolved the task using their medical staff consoles 104. The medical staff consoles 104 respond to this indication by sending a task completion message to the central command computer 109. Accordingly, at blocks 441–442, the central command computer 109 receives the task completion messages and responds by removing the associated task from the appropriate task list. In some embodiments, the central command computer 109 then logs the alert at block 444 as "completed" in the task log shown in FIG. 8 at block 444, and marks the medical staff member as "available" at block 446. The central command computer 109 then returns to block 401 to wait for a new alert and/or to assign the next task from the prioritized list to which that particular staff member is qualified to respond.

Figure 5:
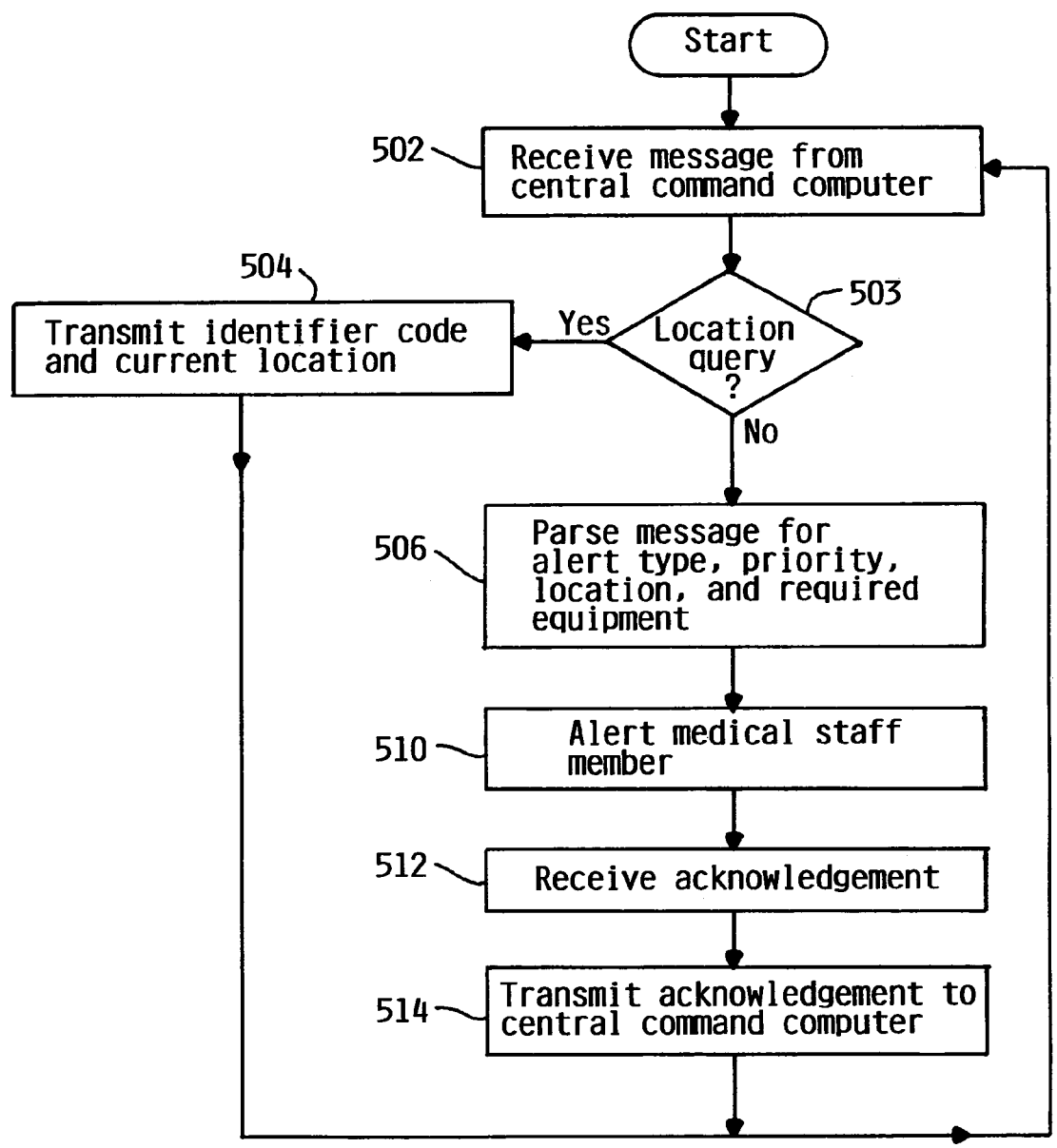
FIG. 5 illustrates the operation of the medical staff console embodiment in FIG. 1.

FIG. 5 illustrates the operation of the medical staff consoles 104 in more detail. At block 502, the console 104 receives a message from the central command computer 109. If this message is a location query, the console 104 responds at block 504 by transmitting a reply message containing its identifier code and its location. If the message is a dispatch message, the console 104 parses the message at block 506 to extract a priority indicator, a patient location, an event code, and a list of medical equipment needed to respond to the event. At block 510–512, the console 104 alerts the medical staff person and receives an acknowledgement of receipt. At block 514, the console 104 transmits a response back to the central command computer 109 indicating that the medical staff person will respond to the event. Next, the medical staff member collects the necessary equipment and supplies to respond to the event using the information received at block 506 and goes to the event location. After successfully handling the event, the medical staff member then resets the medical device and/or patient console 108, which causes the medical device 102 and/or patient console 108 to transmit a message to the central command computer 109 indicating that the task has been handled. The central command computer 109 responds by indicating the medical staff member as ready to handle future events.

FIG. 6 depicts a configuration file 600 for the central command computer 109. The configuration file 600 contains a plurality of event codes 602. Each event code 602 is associated with a name field 604, a priority field 606, a qualified personnel field 608, and a required resources field 610. The name field 604 contains a plain-text name for the event and is used to help the medical personnel quickly identify the event associated with the code 602. The priority field 606 contains a default priority to assign to the event. Life-threatening events are assigned a higher priority than comfort-related events and maintenance/record keeping events. The qualified personnel field 608 contains a list of medical staff (or an identifier associated with the staff member's console 104) that are both qualified and intended to respond to that particular event. Thus, for example, the qualified personnel filed 608 associated with a cardiac arrest may contain identifiers associated with each of the hospital's doctor, and the qualified personnel field associated with a patient vomiting event may contain identifiers associated with the hospital's orderlies. The required resources field 610 contains a list of resources required for the task. Thus, for an "IV Bag is empty" event, the resource field 610 may indicate that the responding person should get a new IV bag from a supply depot. In some cases, the required resource field 610 may also indicate that the event requires more than one medical staff person.

FIG. 7 depicts a status tracking data structure 700 embodiment for each medical staff member and medical device in the hospital. This data structure contains an identifier 702 associated with the staff person or medical device, a name field 704 for the person or device, a current task priority field 706, and a location field 708. The name field 704 contains a plain-text name of the staff person or device. The current task priority field 706 contains the priority associated with the task on which person or device is currently working. The location field 708 contains a code or identifier (e.g., a room number) associated with the area currently occupied by medical staff member or medical device. When the central command computer 109 receives a new task, the central command computer 109 can use the priority field 706 to determine which assets to assign to the task. Thus, for example, if the central command computer 109 receives a cardiac arrest event, it will assign the closest available qualified responder, regardless of what non-interruptible task they are currently working. If the central command computer 109 receives a "Monitor is malfunctioning" message, it will assign the closest qualified responder who is working on a lower priority task. If the central command computer 109 receives a "Patient needs assistance to use the bathroom" message, it assign the task to the next available unassigned qualified staff member. The location field 708 contains the current location of the staff person or medical device. In some embodiments, the central command computer 109 periodically polls the medical devices 102, the medical staff consoles 104, and the patient consoles 108 to request their current location inside the medical facility and updates the location field 708 as the device or console (and thus the associated patient or staff member) leaves one area and move into another area.

Figure 8:
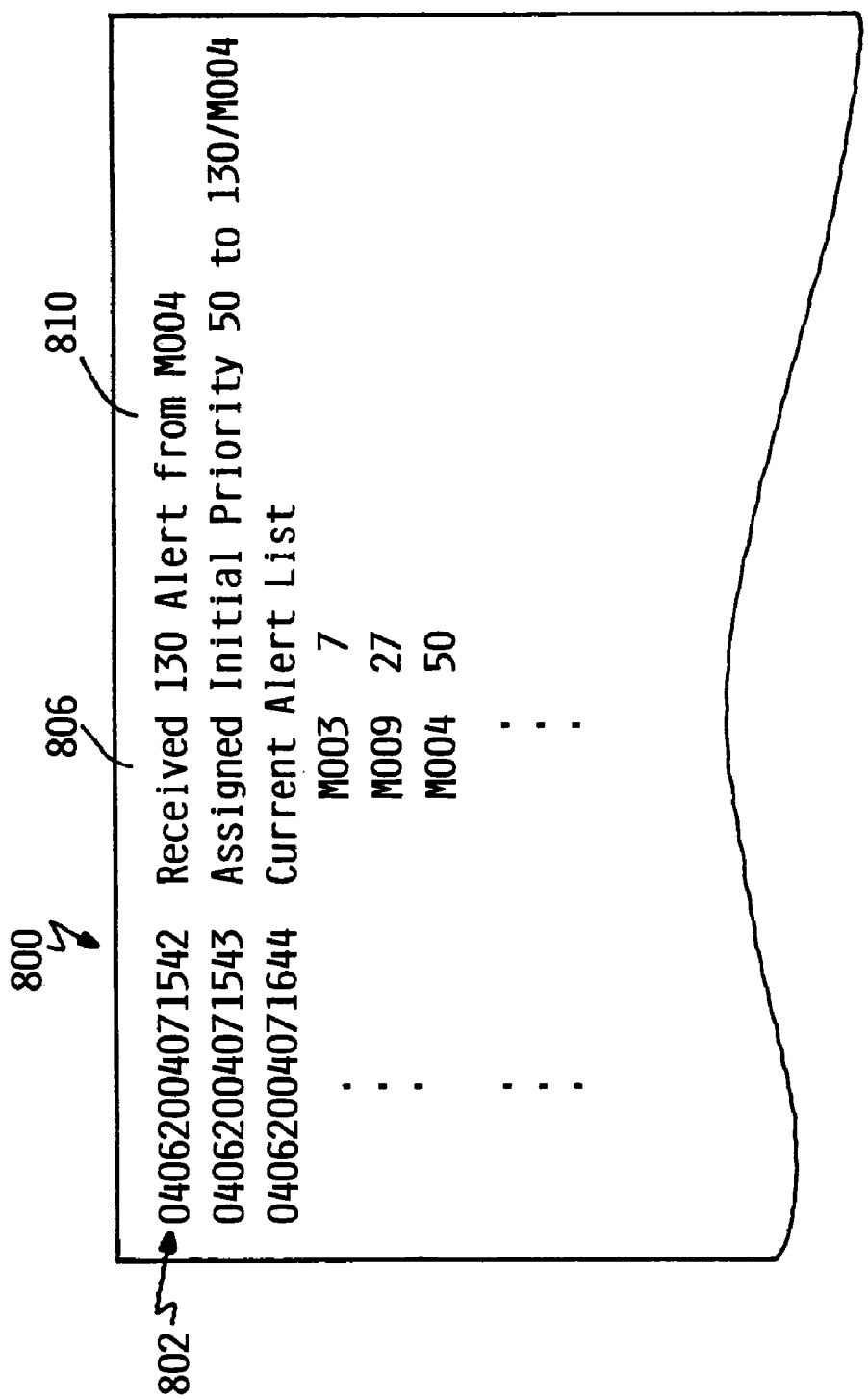
FIG. 8 depicts a journal file embodiment suitable for logging events managed by the central command computer.

FIG. 8 depicts a journal file embodiment 800 suitable for logging events managed by the central command computer 109. This journal file 800 comprises a plurality of log entries 802, each of which a time stamp field 806 and a journal event field 810. The journal file 800 contains entries 802 indicating that the central command computer 109 is about to change to the configuration file 600, the data structures 700, or the priority task list, together with the impending change. The journal file 800 also contains entries 802 indicating that the earlier change was successfully changed. When combined with journaled file system technology, such as that in the JFS file system, and/or database transaction logic, such as that in the DB2 database, these entries 802 allow the configuration files 600, the tracking data structures 700, and the priority task list to be restored to their state at a particular moment in time. This feature may be desirable to recover from a failure of the central command computer 109, for auditing purposes, and as evidence in negligence cases. The JFS file system and DB2 database are both available from International Business Machines, Inc.

Referring again to FIG. 1, the central command computer 109 in this embodiment is a general-purpose programmable computing device. Accordingly, the central processing unit 181 may be any device capable of executing the program instructions stored in main memory 182, and may be constructed from one or more microprocessors and/or integrated circuits. When the central command computer 109 starts, the central processing unit 181 initially executes the program instructions that make up the operating system 187, which manages the physical and logical resources of the computer 109. These resources include the central processing unit 181, the main memory 182, the mass storage interface 185, the display interface 186, the wireless network interface 183, the wired network interface 184, and the system bus 189. Moreover, although the computer 109 in FIG. 1 is shown with only a single processing unit 181 and a single system bus 189, those skilled in the art will appreciate that the present invention may be practiced using a computer 109 that has multiple processing units 181 and/or multiple system buses 189. In addition, the interfaces 183, 184, 185, and 186 may each include their own separate, fully programmed microprocessors, which may be used to off load compute intensive processing from the main processing units 181.

The main memory 182 and the storage devices 140, 142 may be any system capable of storing and retrieving data for the central processing units 181. These systems may utilize virtual addressing mechanisms that allow the computer 109 to behave as if it only has access to a large, single storage entity instead of access to multiple, smaller storage entities such as main memory 182 and a direct access storage device 140. Therefore, while the operating systems 187 and the request management program 188 are shown to reside in main memory 182, those skilled in the art will recognize that these items are not necessarily all completely contained in main memory 182 at the same time, and may even reside in the virtual memory of other computer systems coupled to the computer 109.

The display interface 186 is used to directly connect one or more display units 146 to the computer 109. These display units 146 may be non intelligent (i.e., dumb) terminals, such as a cathode ray tube, or may themselves be fully programmable workstations used to allow IT administrators and users to communicate with one or more of the computer 109. Note, however, that while the display interface 186 is provided to support communication with one or more displays 146, the computer 109 does not necessarily require a display 146 because all needed interaction with users and other processes may occur via network interfaces 183 and 184.

The network interfaces 183 and 184 be any device or system that allows the central control computer 109 to communicate with the medical devices 102, the medical staff consoles 104, and the patient consoles 108, regardless of whether the network connections are made using present day analog and/or digital techniques or via some networking mechanism of the future. Suitable communication mediums include, but are not limited to, a combination of the Internet, intranets, cellular transmission networks, wireless networks using one of the IEEE 802.11x specifications, and the like. Those skilled in the art will appreciate that many different network protocols can be used to implement the communication medium. The Transmission Control Protocol/Internet Protocol ("TCP/IP") is an example of a suitable network protocol for Internet-based communication.

The mobile medical staff consoles 104 and the patient consoles 108 in some embodiments comprise a personal digital assistant ("PDA") with a location detection device and a wireless network interface. These embodiments are desirable because the PDA's typically contain large displays 135 and allow for easy data entry. This display capacity, in turn, may allow the consoles to display information, such as what equipment will be needed to respond to the alert 190, what supplies will be needed to respond to the alert 191, and the time at which the alert was originally generated 192. PDA console embodiments may also be desirable because these devices can also provide access to other information technology systems, such as electronic patient records and the Internet. However, other devices capable of communicating with the central command computer 109 are within the scope of the present invention, including without limitation, pagers, cellular telephones, and custom digital devices.

The medical devices 102 can be any device capable of communicating medical events to the central command computer 109. Embodiments using wireless network interfaces 114 may be particularly desirable because the medical devices can be moved freely around the medical facility. However, wired network interface 114 embodiments are also within the scope of the present invention.

The location detection units 116, 136, and 176 can be any device or system capable of determining the location of the associated device inside the medical facility. Suitable location detection units may use Bluetooth technology, Global Positioning System ("GPS") receivers, detecting proximity to a known physical location (e.g., the emergency signal was received at wireless hub #2, therefore the medical device is located in room 200 or 202), radio frequency identification ("RFID") chip tracking systems, differential signal strength techniques, and/or the systems described in *An Indoor Positioning Service for Bluetooth Ad Hoc Networks* and *Performance of Bluetooth Technologies and their Applications to Location Sensing,* which are herein incorporated by reference in their entirety. Some embodiments may also use a combination of permanent locations (e.g., patient console #3 is always in room 105) and real-time location detection.

The embodiments described with reference to FIGS. 1–8 use a client-server network architecture. These embodiments are desirable because the medical devices, patient consoles 108, and staff consoles 104 can utilize the services of the central command computer 109 without either computer system requiring knowledge of the working details about the other. However, those skilled in the art will appreciate that other network architectures are within the scope of the present invention. Examples of other suitable network architectures include peer to peer architectures, grid architectures, and multi tier architectures. Accordingly, the terms web server and client computer should not be construed to limit the invention to client-server network architectures.

Although the present invention has been described in detail with reference to certain examples thereof, it may be also embodied in other specific forms without departing from the essential spirit or attributes thereof. For example, those skilled in the art will appreciate that the present invention is capable of being distributed as a program product in a variety of forms, and applies equally regardless of the particular type of signal bearing media used to actually carry out the distribution. Examples of suitable signal bearing media include, but are not limited to: (i) information permanently stored on non writable storage media (e.g., read only memory devices within a computer such as CD ROM disks readable by a CD ROM drive); (ii) alterable information stored on writable storage media (e.g., floppy disks within a diskette drive, a CD R disk, a CD RW disk, or hard disk drive); or (iii) information conveyed to a computer by a communications medium, such as through a computer or telephone network, including wireless communications, and specifically includes information downloaded from the Internet and other networks. Such signal bearing media, when carrying computer readable instructions that direct the functions of the present invention, represent embodiments of the present invention.

The accompanying figures and this description depicted and described embodiments of the present invention, and features and components thereof. Those skilled in the art will appreciate that any particular program nomenclature used in this description was merely for convenience, and thus the invention should not be limited to use solely in any specific application identified and/or implied by such nomenclature. Thus, for example, the routines executed to implement the embodiments of the invention, whether implemented as part of an operating system or a specific application, component, program, module, object, or sequence of instructions could have been referred to as a "program", "application", "server", or other meaningful nomenclature. Therefore, it is desired that the embodiments described herein be considered in all respects as illustrative, not restrictive, and that reference be made to the appended claims for determining the scope of the invention.

I claim:

1. A method of responding to medical alerts, comprising:
   receiving a medical alert, the medical alert having an associated alert location;
   detecting a current location for each of a plurality of medical staff members; and
   selecting a medical staff member to respond to the medical alert based at least in part on the distance between the alert location and the current location.

2. The method of claim 1, further comprising receiving a plurality of medical alerts; and selecting a highest priority medical alert from the plurality of medical alerts.

3. The method of claim 1, further comprising determining if the medical alert indicates an emergency situation.

4. The method of claim 1, further comprising tracking an availability status for each of the plurality of medical staff members.

5. The method of claim 4, wherein the selecting is further based at least in part on the availability status for each of the plurality of medical staff members.

6. The method of claim 1, further comprising:
   determining a priority for a plurality of medical alerts; and
   generating a prioritized task list using the priorities for the plurality of medical alerts.

7. The method of claim 6, wherein the selecting is further based at least in part on the prioritized task list.

8. The method of claim 6, further comprising:
   determining if the medical alert is associated with an emergency situation; and
   alerting a medical staff member to the emergency situation.

9. The method of claim 8, wherein the alerted medical staff member was assigned to an alert having a lower priority than alert associated with the emergency situation.

10. The method of claim 6, further comprising periodically increasing the priority of medial alerts in the prioritized task list.

11. The method of claim 1, further comprising logging the medical alert and the selected staff member.

12. A medical alert response system, comprising:
   a medical device that generates an alert message in response to an alert condition, the medical device having a device location associated therewith;
   a plurality of medical alert consoles associated with a plurality of medical staff members, wherein each of the medical alert consoles wirelessly communicates a current location for its associated medical staff member; and
   a dispatcher that receives the medical alert message from the medical device and the current locations from the plurality of medical alert consoles, and selects a medical staff member to respond to the alert based on the proximity between the device location and the staff member's current location.

13. The medical alert response system of claim 12, further comprising a patient console that wirelessly communicates a patient request and a patient location to the dispatcher in response to a patient input.

14. The medical alert response system of claim 12, wherein the medical alert consoles further comprise a display screen adapted to communicate the device location to the associated medical staff member.

15. The medical alert response system of claim 14, wherein the display screen is further adapted to communicate a medical alert type to the associated medical staff member.

16. The medical alert response system of claim 14, wherein the display screen is further adapted to communicate what type of medical equipment and supplies will be needed to respond to the medical alert.

17. The medical alert response system of claim 14, wherein the display is further adapted to communicate a time stamp associated with the medial alert.

18. A computer program product, comprising:
   (a) a computer program encoded on a computer readable medium causing a computer to assign medical assets by performing the acts of:
      receiving a medical alert, the medical alert having an associated alert location;
      detecting a current location for each of a plurality of medical staff members; and
      selecting a medical staff member to respond to the medical alert using the alert location and the current location; and
   (b) a signal bearing media bearing the program.

19. The computer program product of claim 18, wherein the signal bearing media is chosen from the group consisting of information permanently stored on non-writable storage media; alterable information stored on writable storage media; and information conveyed to a computer by a communications medium.

* * * * *